United States Patent
Iatrou et al.

(10) Patent No.: US 7,477,771 B2
(45) Date of Patent: Jan. 13, 2009

(54) METHOD AND SYSTEM FOR EXTRACTING INFORMATION ABOUT THE CARDIAC CYCLE FROM CT PROJECTION DATA

(75) Inventors: Maria Iatrou, Clifton Park, NY (US); Jong Chul Ye, Daejon (KR); Samit Kumar Basu, Niskayuna, NY (US); Bruno Kristiaan Bernard De Man, Clifton Park, NY (US); Peter Michael Edic, Albany, NY (US)

(73) Assignee: Genral Electric Company, Niskayuna, NY (US)

( * ) Notice: Subject to any disclaimer, the term of this patent is extended or adjusted under 35 U.S.C. 154(b) by 774 days.

(21) Appl. No.: 11/003,114

(22) Filed: Dec. 3, 2004

(65) Prior Publication Data

US 2006/0120586 A1 Jun. 8, 2006

(51) Int. Cl.
*G06K 9/00* (2006.01)
*A61B 6/00* (2006.01)
*A61B 5/05* (2006.01)

(52) U.S. Cl. .............................. 382/131; 378/4; 600/425
(58) Field of Classification Search ................. 382/128, 382/129, 130, 131, 132, 133, 134, 190; 378/4, 378/8, 21–27, 101, 901, 69, 90, 92, 95, 98.4, 378/98.6, 98.9, 115; 600/407, 410, 425, 600/324, 450, 479, 481; 424/9.4, 548, 569; 250/363.04
See application file for complete search history.

(56) References Cited

U.S. PATENT DOCUMENTS

| 5,273,040 | A  | * | 12/1993 | Apicella et al. | 600/410 |
| 6,421,552 | B1 | * | 7/2002 | Hsieh | 600/425 |
| 6,434,215 | B1 | * | 8/2002 | Cesmeli | 378/8 |
| 6,580,946 | B2 | * | 6/2003 | Struble | 607/23 |
| 6,798,199 | B2 | * | 9/2004 | Larson et al. | 324/309 |
| 7,058,440 | B2 | * | 6/2006 | Heuscher et al. | 600/428 |
| 2004/0125908 | A1 | | 7/2004 | Cesmeli et al. | 378/4 |

\* cited by examiner

*Primary Examiner*—Abolfazl Tabatabai
(74) *Attorney, Agent, or Firm*—Fletcher Yoder

(57) ABSTRACT

A method for extracting information of a cardiac cycle from projection data is presented. The method provides for acquiring one or more sets of computed tomography (CT) projection data. Further, the method includes analyzing the one or sets of CT projection data to obtain a center of cardiac mass. Also, the method provides for estimating raw motion data representative of the motion of the center of cardiac mass from the one or more sets of CT projection data. In addition, the method includes processing the center of mass through time to extract a motion signal from the raw projection data. Also, the method provides for extracting the periodicity information from the motion signal.

57 Claims, 8 Drawing Sheets

METHOD AND SYSTEM FOR EXTRACTING INFORMATION ABOUT THE CARDIAC CYCLE FROM CT PROJECTION DATA

BACKGROUND

The invention relates generally to the field of medical imaging, and more specifically to the field of imaging dynamic, internal tissue, such as cardiac tissue, by computed tomography.

Non-invasive imaging broadly encompasses techniques for generating images of the internal structures or regions of a person or object that are otherwise inaccessible for visual inspection. For example, non-invasive imaging techniques are commonly used in the industrial field for inspecting the internal structures of parts and in the security field for inspecting the contents of packages, clothing, and so forth. One of the best known uses of non-invasive imaging, however, is in the medical arts where these techniques are used to generate images of organs and/or bones inside a patient that would otherwise not be visible.

One class of non-invasive imaging techniques that may be used in these various fields is based on the differential transmission of X-rays through a patient or object. In the medical context, a simple X-ray imaging technique may involve generating X-rays using an X-ray tube or other source and directing the X-rays through an imaging volume in which the part of the patient to be imaged is located. As the X-rays pass through the patient, the X-rays are attenuated based on the composition of the tissue they pass through. The attenuated X-rays then impact a detector that converts the X-rays into signals that can be processed to generate an image of the part of the patient through which the X-rays passed based on the attenuation of the X-rays.

One such X-ray imaging technique is known as computed tomography (CT). CT imaging systems measure the attenuation of X-ray beams passed through the object from numerous angles. Based upon these measurements, a computer is able to process and reconstruct images of the portions of the object responsible for the radiation attenuation. As will be appreciated by those skilled in the art, these images are computed by processing the angularly displaced projection data to generate cross-sectional and/or three-dimensional reconstructions of the imaged object or region. Such reconstructions may be displayed on a monitor and/or may be printed or reproduced on film.

CT imaging techniques, however, may present certain challenges when imaging dynamic internal tissues, such as the heart. For example, in cardiac imaging, the motion of the heart causes inconsistencies in the projection data, which, after reconstruction, may result in various motion-related image artifacts such as blurring, streaking, or discontinuities. In particular, artifacts may occur during cardiac imaging when projections that are not acquired at the same point in the heart cycle, i.e., the same phase, are used to reconstruct the image or images that comprise the volume rendering.

To avoid the image artifacts associated with cardiac motion, therefore, it is desirable to reconstruct projection data acquired at the same phase into the desired images. This may be done by selective acquisition of the projection data (prospective gating) or by selecting and reconstructing only projection data acquired at the same cardiac phase (retrospective gating). Such gating techniques may utilize a simultaneously acquired electrocardiogram (ECG) signal that is used to acquire select projection data, either prospectively or retrospectively, at a common phase of cardiac motion. In this example, prospective gating refers to modulating data acquisition, such as the X-ray tube output and projection data acquisition, in response to real-time measurement and analysis of the ECG signal, i.e., acquiring only the projections of interest at a specified phase of cardiac motion for reconstruction. Similarly, in this example, retrospective gating refers to using the temporal correspondence between the ECG signal and the acquired projection data, to select only that projection data corresponding to a particular phase of the ECG signal for reconstruction.

However, an ECG signal is a measure of the depolarization and repolarization of the cardiac muscle tissue. While the electrical cardiac events measured by an ECG are generally indicative of cardiac muscle contraction and motion, this electrical activity is still only an indirect indicator of cardiac motion. Because of the indirect nature of this relationship, artifacts may still be present in the images reconstructed using gating techniques that rely upon ECG signals. It is desirable, therefore, to devise methods and apparatus to estimate cardiac motion using acquired CT projection data, without utilizing an ECG device. In addition, examining a patient without disposing electrodes on the patient and connecting the electrodes to an ECG device may advantageously result in increasing patient throughput, which is particularly beneficial in an emergency setting.

BRIEF DESCRIPTION

Briefly, in accordance with an exemplary embodiment of the present technique, a method for extracting information of a cardiac cycle from projection data is presented. The method includes acquiring one or more sets of computed tomography (CT) projection data. Furthermore, the method includes analyzing the one or more sets of CT projection data to obtain a center of cardiac mass. In addition, the method includes estimating raw motion data representative of the motion of the center of cardiac mass from the one or more sets of CT projection data. Also, the method includes processing the raw motion data to extract a motion signal from the raw motion data. The method also includes extracting the periodicity information from the motion signal. Computer-readable medium that afford functionality of the type defined by this method is also provided by the present technique.

According to a further embodiment of the present technique, a method for extracting information of a cardiac cycle from projection data is presented. The method includes acquiring one or more sets of computed tomography (CT) projection data. Additionally, the method includes estimating raw motion data representative of the motion of the center of cardiac mass from the one or more sets of CT projection data. Furthermore, the method includes extracting the periodicity information from the motion signal. Computer-readable medium that afford functionality of the type defined by this method is also provided by the present technique.

In accordance with another embodiment of the present technique, a CT imaging system is presented. The system includes an X-ray source configured to emit a stream of radiation. Further, the system includes an area detector configured to detect the stream of radiation and to generate one or more signals responsive to the stream of radiation, wherein the detector comprises a plurality of detector elements. Additionally, the system includes a system controller configured to rotate the X-ray source and the area detector and to acquire one or more sets of projection data from one or more of the detector elements via a data acquisition system. The system also includes a computer system configured to receive the set of projection data, to analyze the one or more sets of projection data to obtain a center of cardiac mass data, to estimate raw motion data representative of a motion of the center of cardiac mass from the one or more sets of projection data, to extract a motion signal from the raw motion data by separating the motion signal from a noise, and to extract a periodicity information from the motion signal.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
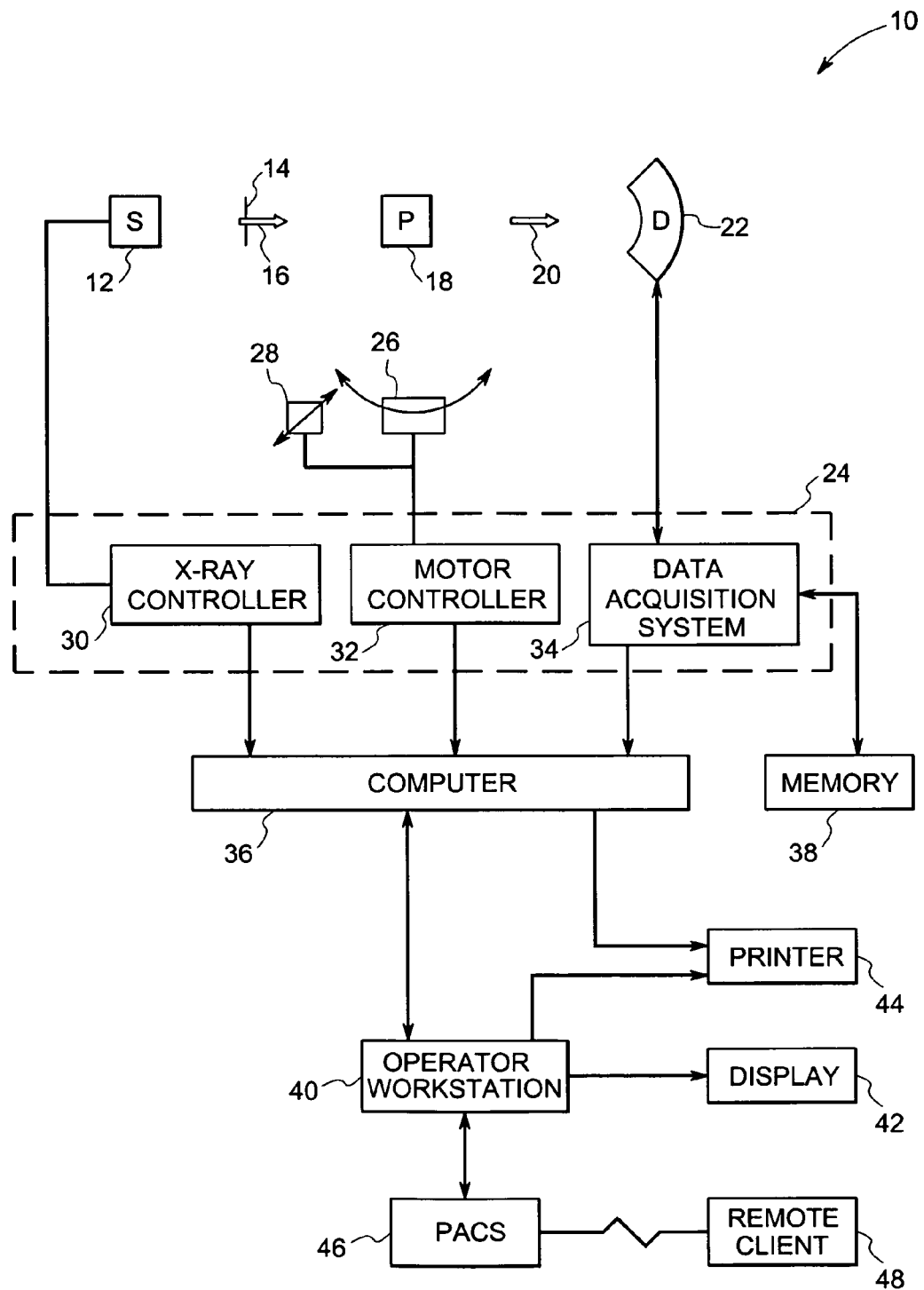
FIG. 1 is a diagrammatical view of an exemplary imaging system in the form of a CT imaging system for use in producing processed images, in accordance with aspects of the present technique.

FIG. 1 illustrates diagrammatically an imaging system 10 for acquiring and processing image data in accordance with the present technique. In the illustrated embodiment, system 10 is a computed tomography (CT) system designed to acquire X-ray projection data, to reconstruct the projection data into an image, and to process the image data for display and analysis in accordance with the present technique. In the embodiment illustrated in FIG. 1, imaging system 10 includes a source of X-ray radiation 12. In one exemplary embodiment, the source 12 of X-ray radiation is an X-ray tube. In other embodiments, the source 12 of X-ray radiation may be one or more solid-state X-ray emitters or, indeed, any other emitter capable of generating X-rays having a spectrum and energy useful for imaging a desired object.

The source 12 of radiation may be positioned near a collimator 14 which shapes the stream of radiation 16 which passes into the imaging volume containing the subject to be imaged, such as the human patient 18. The stream of radiation 16 may be generally fan or cone shaped, depending on the configuration of the detector array, discussed below, as well as the desired method of data acquisition. A portion of the radiation 20 passes through or around the subject and impacts a detector array, represented generally at reference numeral 22. Detector elements of the array produce electrical signals that represent the intensity of the incident X-ray beam. These signals are acquired and processed to reconstruct an image of the features within the subject.

Source 12 is controlled by a system controller 24, which furnishes both power, and control signals for CT examination sequences. Moreover, detector 22 is coupled to the system controller 24, which commands acquisition of the signals generated in the detector 22. The system controller 24 may also execute various signal processing and filtration functions, such as for initial adjustment of dynamic ranges, interleaving of digital image data, and so forth. In general, system controller 24 commands operation of the imaging system to execute examination protocols and to process acquired data. In the present context, system controller 24 also includes signal processing circuitry, typically based upon a general purpose or application-specific digital computer, associated memory circuitry for storing programs and routines executed by the computer, as well as configuration parameters and image data, interface circuits, and so forth.

In the embodiment illustrated in FIG. 1, system controller 24 via a motor controller 32 is coupled to a rotational subsystem 26 and a linear positioning subsystem 28. In one embodiment, the rotational subsystem 26 enables the X-ray source 12, collimator 14 and the detector 22 to be rotated one or multiple turns around the patient 18. In other embodiments, the rotational subsystem 26 may rotate only one of the source 12 or the detector 22 or may differentially activate various X-ray emitters and/or detector elements arranged in a ring about the imaging volume. In embodiments in which the source 12 and/or detector 22 are rotated, the rotational subsystem 26 may include a gantry. Thus, the system controller 24 may be utilized to operate the gantry. The linear positioning subsystem 28 enables the patient 18, or more specifically a patient table, to be displaced linearly. Thus, the patient table may be linearly moved within the gantry to generate images of particular areas of the patient 18.

Additionally, as will be appreciated by those skilled in the art, the source of radiation may be controlled by an X-ray controller 30 disposed within the system controller 24. Particularly, the X-ray controller 30 is configured to provide power and timing signals to the X-ray source 12.

Further, the system controller 24 is also illustrated comprising a data acquisition system 34. In this exemplary embodiment, the detector 22 is coupled to the system controller 24, and more particularly to the data acquisition system 34. The data acquisition system 34 receives data collected by readout electronics of the detector 22. The data acquisition system 34 typically receives sampled analog signals from the detector 22 and converts the data to digital signals for subsequent processing by a computer 36.

The computer 36 typically is coupled to or incorporates the system controller 24. The data collected by the data acquisition system 34 may be transmitted to the computer 36 for subsequent processing and reconstruction. The computer 36 may comprise or communicate with a memory 38 that can store data processed by the computer 36 or data to be processed by the computer 36. It should be understood that any type of memory configured to store a large amount of data might be utilized by such an exemplary system 10. Moreover, the memory 38 may be located at the acquisition system or may include remote components, such as network accessible memory media, for storing data, processing parameters, and/or routines for implementing the techniques described below.

The computer 36 may also be adapted to control features enabled by the system controller 24, i.e., scanning operations and data acquisition. Furthermore, the computer 36 may be configured to receive commands and scanning parameters from an operator via an operator workstation 40 typically equipped with a keyboard and other input devices (not shown). An operator may thereby control the system 10 via the input devices. Thus, the operator may observe the reconstructed image and other data relevant to the system from computer 36, initiate imaging, and so forth.

A display 42 coupled to the operator workstation 40 may be utilized to observe the reconstructed image. Additionally, the scanned image may also be printed by a printer 44 which may be coupled to the operator workstation 40. The display 42 and printer 44 may also be connected to the computer 36, either directly or via the operator workstation 40. Further, the operator workstation 40 may also be coupled to a picture archiving and communications system (PACS) 46. It should be noted that PACS 46 might be coupled to a remote system 48, radiology department information system (RIS), hospital information system (HIS) or to an internal or external network, so that others at different locations may gain access to the image data.

It should be further noted that the computer 36 and operator workstation 40 may be coupled to other output devices, which may include standard, or special purpose computer monitors and associated processing circuitry. One or more operator workstations 40 may be further linked in the system for outputting system parameters, requesting examinations, viewing images, and so forth. In general, displays, printers, workstations, and similar devices supplied within the system may be local to the data acquisition components, or may be remote from these components, such as elsewhere within an institution or hospital, or in an entirely different location, linked to the image acquisition system via one or more configurable networks, such as the Internet, virtual private networks, and so forth.

Figure 2:
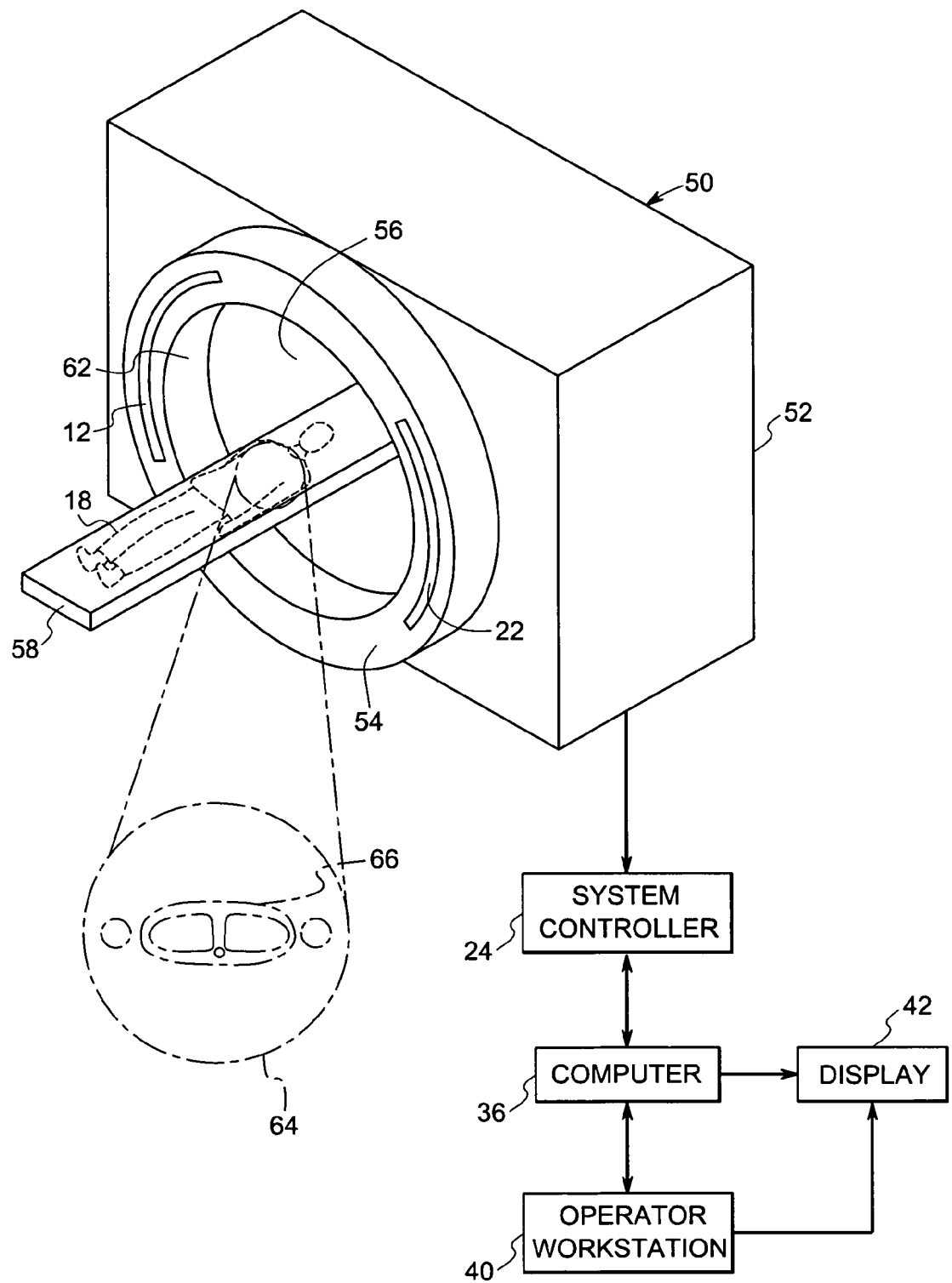
FIG. 2 is a diagrammatical view of a physical implementation of the CT system of FIG. 1, in accordance with aspects of the present technique.

As noted above, an exemplary imaging system utilized in a present embodiment may be a CT scanning system 50, as depicted in greater detail in FIG. 2. The CT scanning system 50 may be a multi-slice detector CT (MDCT) system that offers a wide array of axial coverage, high gantry rotational speed, and high spatial resolution. Alternately, the CT scanning system 50 may be a volumetric CT (VCT) system utilizing a cone-beam geometry and an area detector to allow the imaging of a volume, such as an entire internal organ of a subject, at high or low gantry rotational speeds. The CT scanning system 50 is illustrated with a frame 52 and a gantry 54 that has an aperture 56 through which a patient 18 may be moved. A patient table 58 may be positioned in the aperture 56 of the frame 52 and the gantry 54 to facilitate movement of the patient 18, typically via linear displacement of the table 58 by the linear positioning subsystem 28 (see FIG. 1). The gantry 54 is illustrated with the source of radiation 12, such as an X-ray tube that emits X-ray radiation from a focal point 62. For cardiac imaging, the stream of radiation is directed towards a cross section of the patient 18 including the heart.

In typical operation, X-ray source 12 projects an X-ray beam from the focal point 62 and toward detector array 22. The collimator 14 (see FIG. 1), such as lead or tungsten shutters, typically defines the size and shape of the X-ray beam that emerges from the X-ray source 12. The detector 22 is generally formed by a plurality of detector elements, which detect the X-rays that pass through and around a subject of interest, such as the heart or chest. Each detector element produces an electrical signal that represents the intensity of the X-ray beam at the position of the element at the time the beam strikes the detector. The gantry 54 is rotated around the subject of interest so that a plurality of radiographic views may be collected by the computer 36.

Thus, as the X-ray source 12 and the detector 22 rotate, detector 22 collects data of the attenuated X-ray beams. Data collected from the detector 22 then undergoes pre-processing and calibration to condition the data to represent the line integrals of the attenuation coefficients of the scanned objects. The processed data, commonly called projections, may then be filtered and backprojected to formulate an image of the scanned area. A formulated image may incorporate, in certain modes, less or more than 360 degrees of projection data.

Once reconstructed, the image produced by the system of FIGS. 1 and 2 reveals internal features 66 of the patient 18. In traditional approaches for the diagnosis of disease states, and more generally of medical conditions or events, a radiologist or physician would consider the reconstructed image 64 to discern characteristic features of interest. In cardiac imaging, such features 66 include coronary arteries or stenotic lesions of interest, and other features, which would be discernable in the image, based upon the skill and knowledge of the individual practitioner. Other analyses may be based upon capabilities of various CAD algorithms.

Reconstruction of images 64 of dynamically moving tissue may present particular concerns. Projection data sets that encompass data points acquired at different phases of the cardiac cycle may result in discontinuities or motion related artifacts in a reconstructed image or a rendered volume comprising a sequence of adjacent images. Therefore, in the context of cardiac imaging, it is generally desirable to acquire or select projection data from a common cardiac phase, such as during a phase in which motion is minimized.

Figure 3:
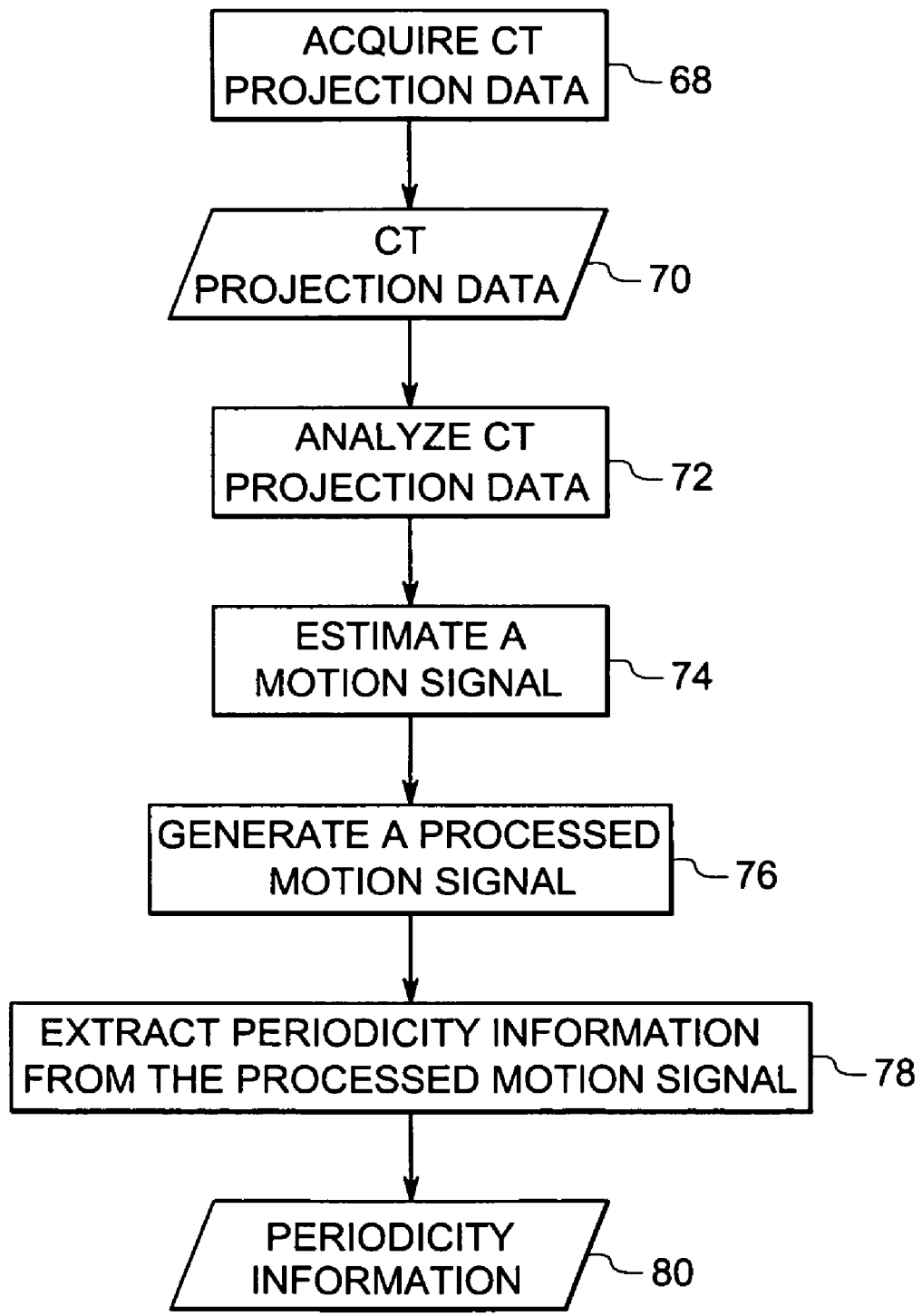
FIG. 3 is a flow chart depicting one embodiment of the present technique, in accordance with aspects of the present technique.

As will be appreciated by one skilled in the art, some cardiac CT reconstruction algorithms employ concurrently recorded ECG signals to aid in the reconstruction. However, in accordance with the present technique, cardiac (or other) motion may be derived from the CT projection data itself. Referring now to FIG. 3, a flow chart depicting steps for extracting information about the cardiac cycle from CT projection data, in accordance with the present technique, is illustrated. The extracted data regarding the cardiac cycle may be advantageously utilized to complement or replace an ECG signal, thereby increasing patient comfort and reducing costs.

In the example depicted by FIG. 3, the method for extracting information about the cardiac cycle from the CT projection data begins at step 68, where CT projection data 70 is acquired for the patient 18 (see FIG. 1), such as via the CT scanning system of FIG. 1. The CT projection data 70 may be analyzed to extract information regarding the cardiac cycle at step 72. For example, according to aspects of the present technique, a center of mass of the object being scanned, such as the heart, may be computed utilizing the CT projection data 70 and the center of mass may be continuously tracked over a predetermined period of time to determine the cardiac motion over time. As will be appreciated by one skilled in the art, the displacement of the center of the mass of the object being scanned follows the periodicity of the cardiac motion. Hence, the periodicity information 80 of the cardiac motion may be extracted by tracking the center of mass data over time, as will be described hereinafter.

At step 74 raw motion data representative of the motion of the center of cardiac mass over a predetermined period of time may be estimated. Further, at step 76, the raw motion data may be processed to extract a motion signal from the noise in the raw motion data. In this embodiment, the motion signal may be a signal representative of the displacement of the center of mass of the object being scanned. Further, in this embodiment the predetermined period of time may represent the duration of a scan. At step 78 the periodicity information 80 may be extracted from the motion signal.

As noted above, the center of mass for a projection image may be employed to estimate the center of mass of the object being scanned. For instance, at step 72, the acquired CT projection data 70 may be analyzed to obtain an estimate of the center of mass of the slice being currently scanned. In one embodiment, the estimation of the center of mass data of a slice being currently scanned is described with reference to a parallel beam geometry of the CT projection data 70, as illustrated in FIG. 4.

Figure 4:
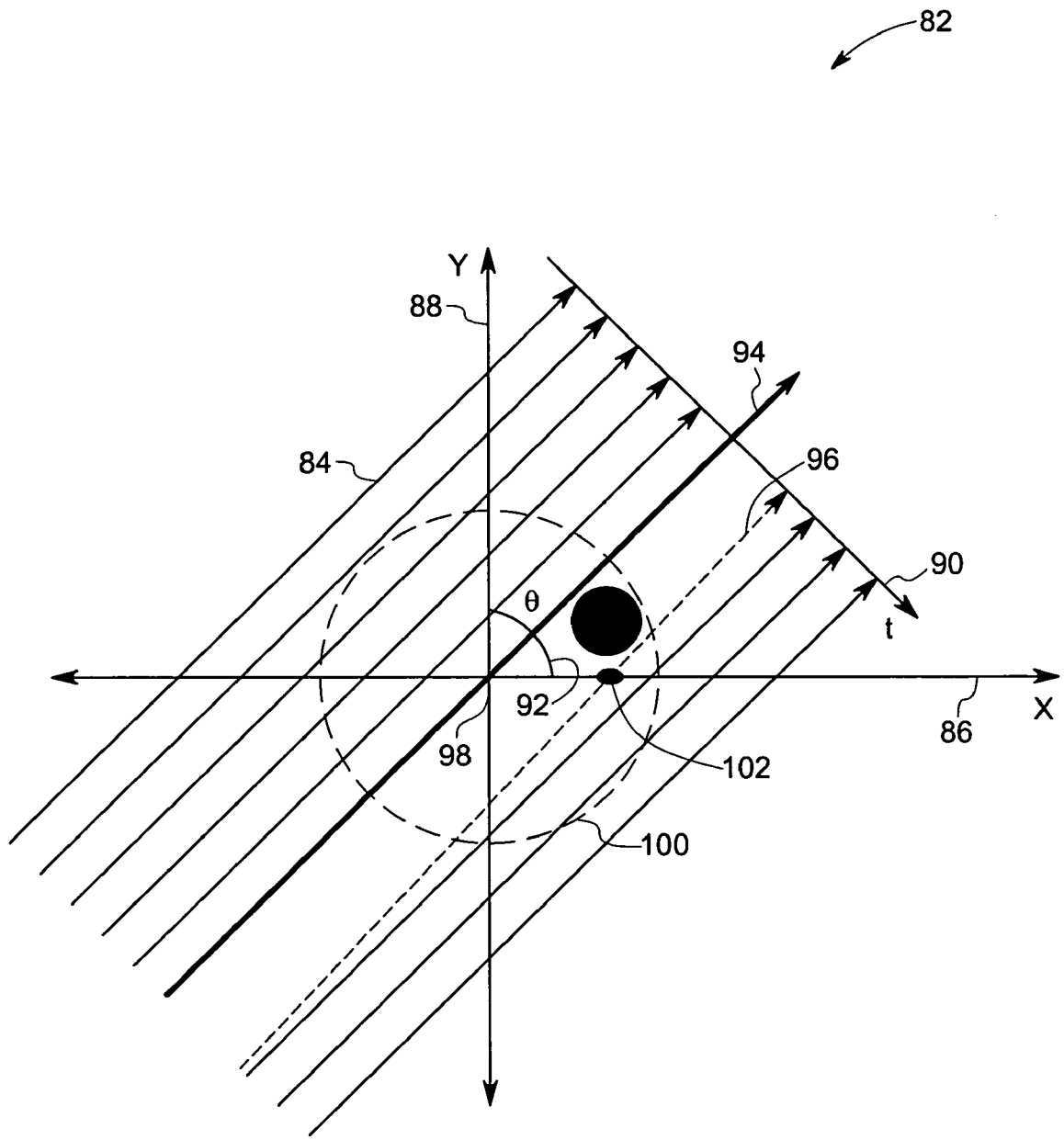
FIG. 4 is a diagrammatical illustration of a parallel beam geometry of the CT projection data, in accordance with aspects of the present technique.

Referring to FIG. 4, a parallel beam geometry 82 of CT projection data is illustrated. As will be appreciated by one skilled in the art, in the parallel beam geometry 82, the projection measurements are acquired using parallel X-rays 84 or are processed to correspond to an acquisition employing such parallel X-rays. In FIG. 4, the parallel rays 84 are plotted along an x-axis 86 and a y-axis 88. Further, t 90 represents a radial location of a detector. In addition, θ 92 represents a projection angle. Also, reference numeral 94 represents a projection center. The projection center of mass is represented by reference numeral 96. Further, reference numeral 98 may represent a center of rotation 98. In addition, f(x,y) 100 may represent the object. Further, reference numeral 102 represents a center of mass of the object being scanned.

In the case of the parallel beam geometry 82 depicted in FIG. 4, the parallel beam projection may be given by:

$$P_\theta(t) = \int\int f(x,y)\delta(x\cos\theta + y\sin\theta - t)dxdy \qquad (1)$$

where θ represents a projection angle, t represents a detector radial location, and f(x,y) the object.

From equation (1), $$\int tP_\theta(t)dt = \cos\theta \int\int xf(x,y)dxdy + \sin\theta \int\int yf(x,y)dxdy \qquad (2)$$

From equation (2), it may be inferred that the center of mass of the object function projects onto the center of mass of the corresponding parallel projection:

$$\bar{t}(\theta) = \frac{\int tP_\theta(t)dt}{\int P_\theta(t)dt} = \bar{x}\cos\theta + \bar{y}\sin\theta \qquad (3)$$

and $$\bar{x} = \frac{\int\int xf(x,y)dxdy}{\int\int f(x,y)dxdy},$$

$$\bar{y} = \frac{\int\int yf(x,y)dxdy}{\int\int f(x,y)dxdy} \qquad (4)$$

where θ represents the projections angle, t is the detector radial location, $\bar{x}$ and $\bar{y}$ are the projections of center of mass on axes x and y respectively as defined in equation (4) and $\bar{t}$ is the center of mass of the projection data at angle θ.

From equation (3), it may be observed that if the object being scanned moves relative to the X-rays 84 and/or detector, the corresponding center of mass also changes with time. Similarly, the projected center of mass data $\bar{t}$ also changes with time, and hence along view angle θ. Therefore, the measured projection center of mass $\bar{t}(\theta)$ may be employed to estimate the object center of mass and, hence, to extract the object motion.

The estimate of the object center of mass $(\bar{x}, \bar{y})$ may be computed employing least square fitting from a distinct set of projection angles θ's. More specifically, equation (3) may be sampled at N≧2 consecutive views:

$$\bar{t}(\theta_i) = \bar{x}\cos\theta_i + \bar{y}\sin\theta_i \qquad (5)$$

where i=1, 2, ... N.

In this embodiment, therefore, the center of mass estimate $(\bar{x}, \bar{y})$ may be given by the least square solution of the system of N linear equations.

However, as will be appreciated by those of ordinary skill in the art, many CT systems employ fan beam geometry as opposed to parallel beam geometry. In accordance with aspects of the present technique, projections acquired using a fan beam geometry may be transformed to correspond to an acquisition using a parallel beam geometry 82 prior to further processing. Hence, it may be desirable to derive a center of mass relationship for the fan beam geometry by investigating the relationship between the parallel beam geometry 82 and the fan beam geometry.

Figure 5:
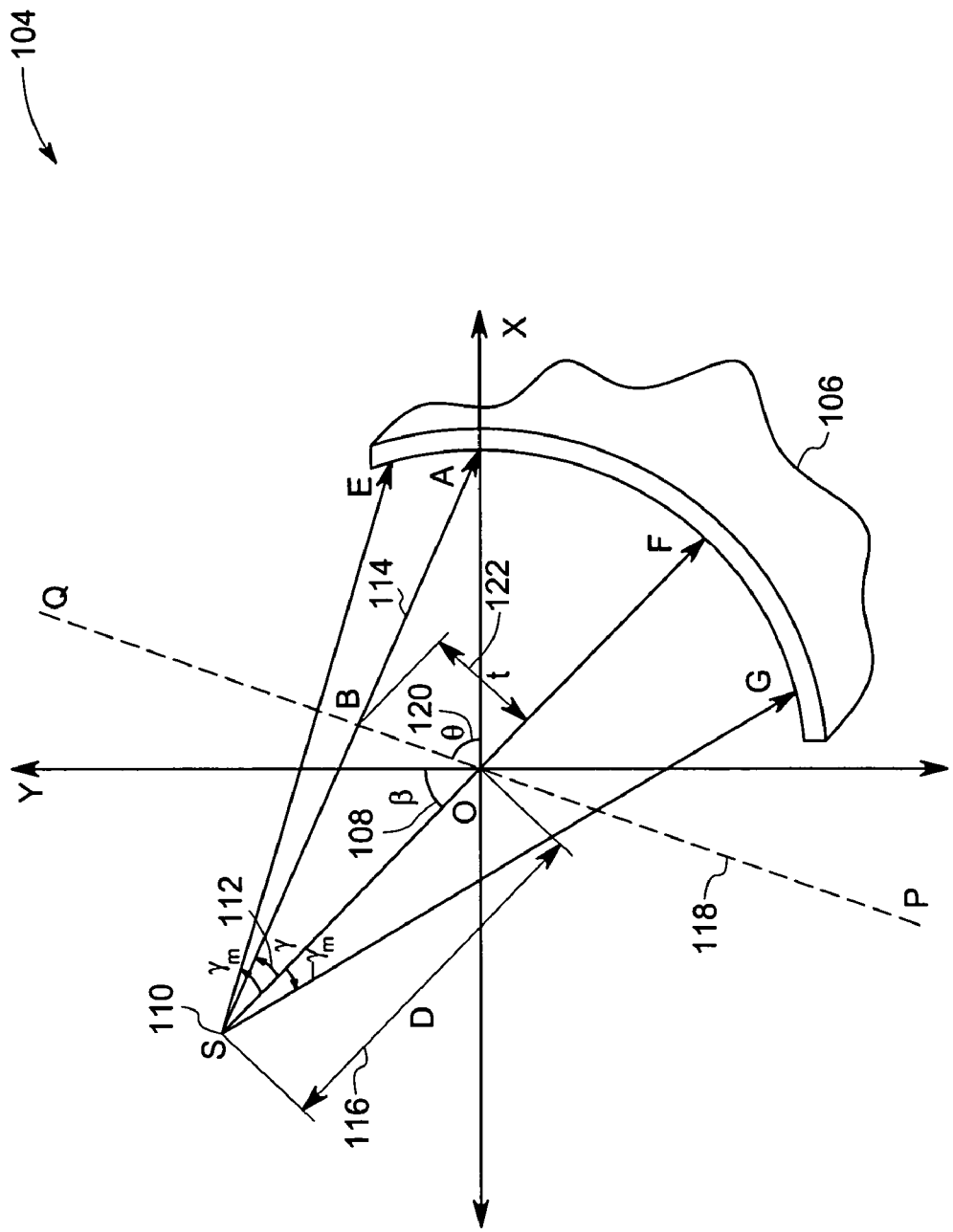
FIG. 5 is a diagrammatical illustration of a fan beam geometry of the CT projection data, in accordance with aspects of the present technique.

FIG. 5 illustrates an exemplary embodiment of a fan beam geometry 104. Let $R_\beta(\gamma)$ 106 denote a fan projection as illustrated in FIG. 5, where β 108 is an angle that the source S 110 makes with a reference axis. The angle γ 112 gives the location of a ray, such as the ray SA 114, within the fan 106. Given the ray SA 114, if the projection data were generated along a set of parallel rays, then the ray SA 114 would belong to a parallel projection $P_\theta(t)$, for θ120 and t 122 given by:

$$\theta = \beta + \gamma$$

and $$t = D\sin\gamma \qquad (6)$$

where D 116 is the distance from the source to the isocenter of the imaging volume.

Employing equation (6) and the polar coordinate transform (x,y):

$$x = r\cos\phi$$

and $$y = r\sin\phi \qquad (7)$$

Equation (1) may be transformed to $$R_\beta(\gamma) = P_{\beta+\gamma}(D\sin\gamma) \qquad (8)$$

$$= \int_0^{2\pi}\int_0^\infty rf(r,\phi)\delta(r(\cos(\alpha+\beta-\phi)-D\sin\gamma))\,dr\,d\phi$$

In order to derive the moment of the fan-beam projection 104, the fan beam data is weighted along the virtual plane QP 118:

$$\int_{-\gamma_m}^{\gamma_m}(\sin\gamma)R_\beta(\gamma)\,d\gamma = \qquad (9)$$

$$\int_{-\gamma_m}^{\gamma_m}\int_0^{2\pi}\int_0^\infty (\sin\gamma)rf(r,\phi)\delta(r\cos(\alpha+\beta-\phi)-D\sin\gamma)\,dr\,d\phi\,d\gamma$$

Employing the following change of variables:

$$L\cos\gamma' = D + r\sin(\beta-\phi)$$

and $$L\sin\gamma' = r\cos(\beta-\phi) \qquad (10)$$

Substituting equation (10) in equation (8):

$$D\sin\gamma - r\cos(\alpha+\beta-\phi) = D\sin\gamma - r[\cos\gamma\cos(\beta-\phi) - \sin\gamma\sin(\beta-\phi)] = \sin\gamma(D + r\sin(\beta-\phi)) - \cos\gamma(r\cos(\beta-\phi)) = L\sin\gamma\cos\gamma' - L\cos\gamma\sin\gamma' = L\sin(\gamma-\gamma')$$ (11)

Therefore, employing equation (11), equation (9) may be written as:

$$\int_{-\gamma_m}^{\gamma_m}(\sin\gamma)R_\beta(\gamma)d\gamma =$$ (12)

$$\int_{-\gamma_m}^{\gamma_m}\int_0^{2\pi}\int_0^\infty (\sin\gamma)rf(r,\phi)\delta(L\sin(\gamma-\gamma'))dr\,d\phi\,d\gamma$$

Generally, in most CT systems, the fan angle $\gamma$ 112 is less than $\pi$, that is, $$\gamma_m \leq \frac{\pi}{2}.$$

Therefore, equation (12) may be simplified to be:

$$\int_{-\gamma_m}^{\gamma_m}(\sin\gamma)R_\beta(\gamma)d\gamma = \int_0^{2\pi}\int_0^\infty \frac{(\sin\gamma')}{|L\cos(\gamma-\gamma')|}rf(r,\phi)dr\,d\phi\,d\gamma$$ (13)

$$= \int_0^{2\pi}\int_0^\infty \frac{(\sin\gamma')}{L}rf(r,\phi)dr\,d\phi\,d\gamma$$

Employing the change of variables of equation (10):

$$L = \sqrt{D^2 + r^2 + 2rD\sin(\beta-\phi)}$$ (14)

and $$\sin\gamma' = \frac{r}{L}\cos(\beta-\phi)$$

Substituting equation (14) in equation (13):

$$\int_{-\gamma_m}^{\gamma_m}(\sin\gamma)R_\beta(\gamma)d\gamma = \int_0^{2\pi}\int_0^\infty \frac{r^2\cos(\beta-\phi)f(r,\phi)}{D^2 + r^2 + 2rD\sin(\beta-\phi)}dr\,d\phi$$ (15)

However, since $D^2 + r^2 \geq 2rD$, the following Taylor series expansion may be employed:

$$\frac{1}{D^2 + r^2 + 2rD\sin(\beta-\phi)} = \frac{1}{D^2+r^2}\left\{1 + \sum_{n=1}^{\infty}\left(-\frac{2Dr\sin(\beta-\phi)}{D^2+r^2}\right)^n\right\}$$ (16)

Therefore, $$\int_{-\gamma_m}^{\gamma_m}(\sin\gamma)R_\beta(\gamma)d\gamma =$$ (17)

$$\int_0^{2\pi}\int_0^\infty \frac{r^2\cos(\beta-\phi)f(r,\phi)}{D^2+r^2}dr\,d\phi\left[1 + \sum_{n=1}^{\infty}\left(-\frac{2Dr\sin(\beta-\phi)}{D^2+r^2}\right)^n\right]$$

Using polar to Cartesian coordinate transform:

$$\int_{-\gamma_m}^{\gamma_m}\int_0^{2\pi}\frac{r^2\cos(\beta-\phi)f(r,\phi)}{D^2+r^2}dr\,d\phi =$$ (18)

$$\cos\beta\int\frac{xf(x,y)}{D^2+x^2+y^2}dx + \sin\beta\int\frac{yf(x,y)}{D^2+x^2+y^2}dy$$

Further, if $D^2+r^2 \gg 2Dr$, the higher order term in the right hand side of equation (15) may be neglected. Hence:

$$\int_{-\gamma_m}^{\gamma_m}(\sin\gamma)R_\beta(\gamma)d\gamma \approx \bar{x}\cos\beta + \bar{y}\sin\beta$$ (19)

where, $$\bar{x} = \int\frac{xf(x,y)}{D^2+x^2+y^2}dx \text{ and}$$

$$\bar{y} = \int\frac{yf(x,y)}{D^2+x^2+y^2}dy$$ (20)

Therefore, it may be inferred that there exists an approximate center of mass relationship between the waveform and the image domain for the fan beam geometry 104 in addition to the parallel beam geometry 82. As described hereinabove, equation (3) may be employed to compute the center of mass data for the parallel beam geometry 82 of FIG. 4. In a similar fashion, equation (20) may be utilized to compute the center of mass data for the fan beam geometry 104 of FIG. 5.

In accordance with aspects of the present technique, methods, such as use of the Helgason-Ludwig consistency conditions, may be employed to generate motion information from the acquired projection data. As will be appreciated by one skilled in the art, the Helgason-Ludwig consistency conditions state that spatial moments $M_k$ of projections may be obtained by employing the following equation:

$$M_k = \int s^k Rf(s,\theta)ds$$ (21)

where $M_k$ is the $k^{th}$ order moment, k is a positive integer representative of the order of the moment, s is the detector element, $\theta$ is the view angle, f is the object function and R is the Radon transform. Further, $M_k$ is a homogeneous polynomial of degree k in sin $\theta$ and cos $\theta$.

In accordance with aspects of the present technique, the estimate of the center of mass of each of the one or more sets of CT projection data may be computed via the Helgason-Ludwig moments associated with each of the one or more sets of CT projection data. In particular, the zero order moment may be representative of the mass of the object being scanned while the first order moment may be representative of the center of mass of the object being scanned. In other words, the change in the location of the center of mass over time, as determined from the first order moments, may be used to derive the motion of the center of mass of the heart within an image slice over that period of time. For instance, for each set of CT projection data, a first order moment may be repeatedly computed to allow the center of mass within the respective images to be tracked over time. Periodicity information pertaining to the cardiac cycle may then be extracted from the derived center of mass information for the one or more cardiac image slices over time.

As will be appreciated by one skilled in the art, the raw motion data, such as the center of mass data, may be contaminated by interfering signals or noises. Specifically, the center of mass data may contain structural variation along a scanning direction attributable to the linear displacement associated with a helical acquisition protocol. Furthermore, due to non-linearities, such as beam hardening, and non-linear partial volume, the center of mass data may be contaminated by harmonics with fundamental frequency equal to the gantry rotational frequency. The above mentioned interference signals or noise are generally non-stationary in nature. Hence, it may be desirable to extract a clean cardiac motion signal that is representative of the cardiac motion, from the initial, noisy, center of mass motion data.

Therefore, in one embodiment, the estimates of the center of mass may be processed to remove noise associated with low frequency fluctuations to extract a clean, cardiac motion signal. For instance, the noise in the estimated center of mass data may be removed via a low pass filter. Furthermore, a short-time Fourier transform (STFT) may be employed to extract the motion signal from the noisy signal, such as the center of mass data. Also, a continuous wavelet transform may be employed to extract the motion signal from the noise in order to generate a "clean" waveform. Alternatively, a Reassigned STFT may be employed to extract the motion signal from the raw motion data.

As will be appreciated by one skilled in the art, the cardiac motion signal based on the derived center of mass information may vary due to variations in the patient's heart rate during the image acquisition process. Accordingly, in an exemplary embodiment of the present technique one or more of the above mentioned techniques, such as the short-time Fourier transform, the continuous wavelet transform and the Reassigned STFT, or a combination thereof may be employed to extract the cardiac motion signal from the derived center of mass information based on the heart rate of the patient at different points in time. In particular, in this embodiment, a suitable transform or technique is selected and employed based upon the heart rate of the patient during the acquisition of the projection data being processed.

Figure 6:
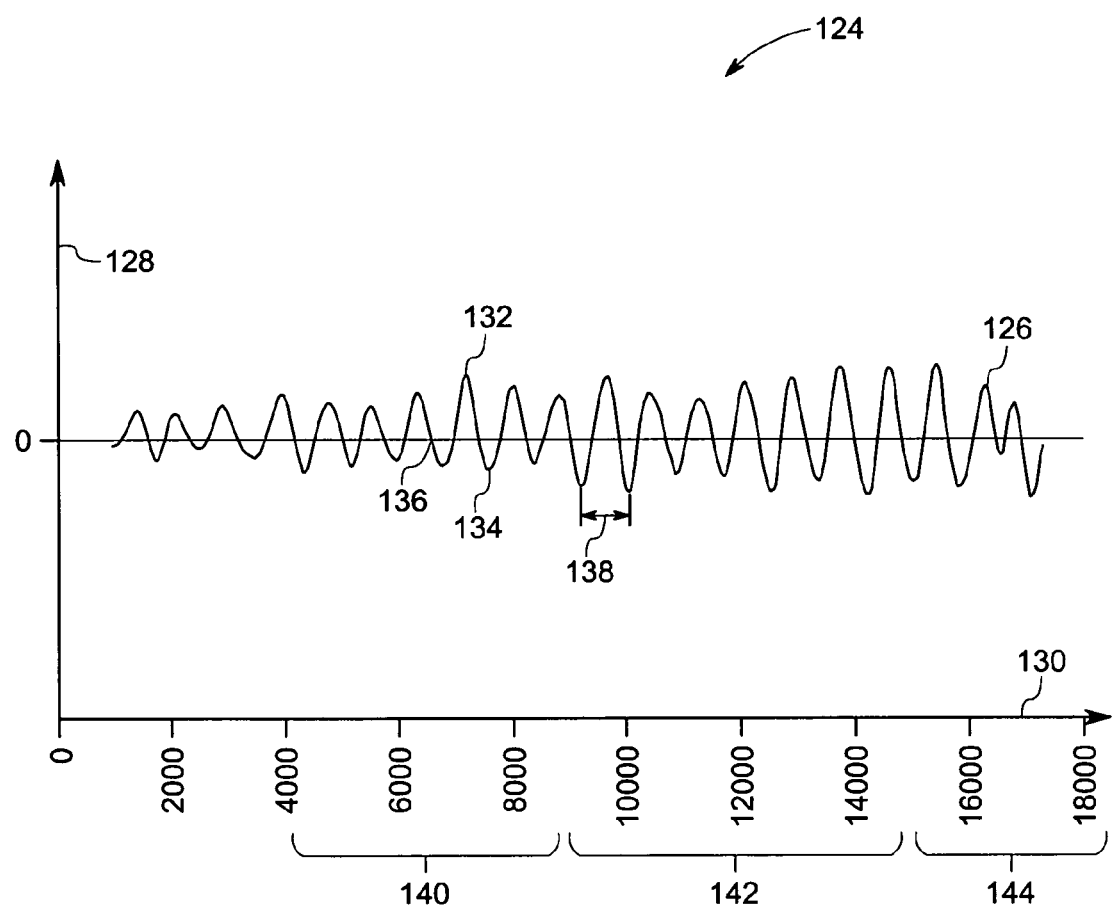
FIG. 6 is a representation of a waveform derived from projection data, in accordance with aspects of the present technique.

For example, FIG. 6 illustrates a waveform 124 representative of the tracking of the center of mass data over a period of time. In FIG. 6, the extracted motion of the center of mass 126 is illustrated, where the amplitude 128 of extracted motion of the center of mass 126 is plotted against time 130. Further, reference numeral 132 represents a maxima and reference numeral 134 represents a minima of the waveform, and presumably an extreme of the motion of the center of mass. Additionally, reference numeral 136 represents a zero crossing. A period of the cardiac cycle may be represented by reference numeral 138. In accordance with aspects of the present technique, a method best suited for deriving the cardiac motion at the given point in time may be selected for extracting the cardiac motion from the center of mass information.

Depending on the information to be extracted from the motion signal wavelet analysis and wavelet coefficients may be employed. For example, the motion signal during a time period represented by reference numeral 140 that may include a trend due to anatomy changes in a longitudinal direction may be de-trended by reconstructing the trend of the motion signal during time period 140 by utilizing only wavelet coefficients corresponding to approximation at certain levels. Employing a similar approach, the motion signal during the time period 140 may be de-noised either by zeroing the detail coefficients or by modifying all coefficients appropriately. Another suggested purpose of wavelet analysis is for the removal of a signal with frequency component equal to the gantry rotation frequency, which may corrupt the signal of interest. Similarly, for periods represented by reference numerals 142 and 144, one of the above mentioned techniques or different combinations thereof may be employed to extract the cardiac motion signal based upon the varying heart rate.

As previously mentioned with reference to FIG. 3, the periodicity information may be extracted from the cardiac motion signal generated by removing the noise component from the tracked center of mass data. In accordance with aspects of the present technique, a first order derivative and/or a second order derivative may be computed for the tracked center of mass data. The first order derivative and the second order derivative may then be employed to identify inflection points of the tracked center of mass data which may be indicative of particular phases of cardiac motion, such as diastole or systole. For instance, the inflection points of the tracked center of mass data may include the maxima 132 and the minima 134 as illustrated in FIG. 6. Additionally, the inflection points of the tracked center of mass data may also include a zero crossing 136. Using these inflections changes, maxima, minima, and/or crossings, a cardiac period may be derived.

Furthermore, the different periods of the cardiac cycle, such as diastole and systole, may be related to corresponding inflections, maxima, minima, or crossings within the waveform such that one or more phases of interest may be determined from the projection data. In this manner, only that image data acquired at the desired phase or phases of interest may be reconstructed to generate a cardiac image, thereby reducing or eliminating artifacts attributable to cardiac motion. For example, in one embodiment, the volume of the heart may be reconstructed using projection data acquired at a derived inflection point, minima, maxima, or crossing or at some interval or percentage of a cardiac period from such a point. For instance, in one embodiment, projection data is selected for reconstruction, which was acquired at an offset of 70% of a cardiac period from each maximum of the waveform describing the center of mass over time.

According to another aspect of the present technique, an alternate method of extracting information about the cardiac cycle from the CT projection data is presented. In accordance with an exemplary embodiment of the present technique, a motion signal is extracted from the raw motion data, such as the tracked center of mass data. Specifically, the motion signal may be extracted from the raw motion data via principal component analysis.

As will be appreciated by one of ordinary skill in the art, in this embodiment, data is rearranged in principal component space before further analysis, such as cluster analysis, is performed. Analysis of data that has been transformed into principal component space is referred to as principal component analysis, or PCA. In other words, data may be transformed from the original axes to the principal axis prior to further analysis.

Further, a principal axis of a hyperellipse is defined as the axis along which the data in n-dimensional space is primarily distributed. In two dimensions, the first principal axis is the major axis of the hyperellipsoid that best fits the data set. The first principal axis, therefore, is the direction in which the data is primarily distributed.

Figure 7:
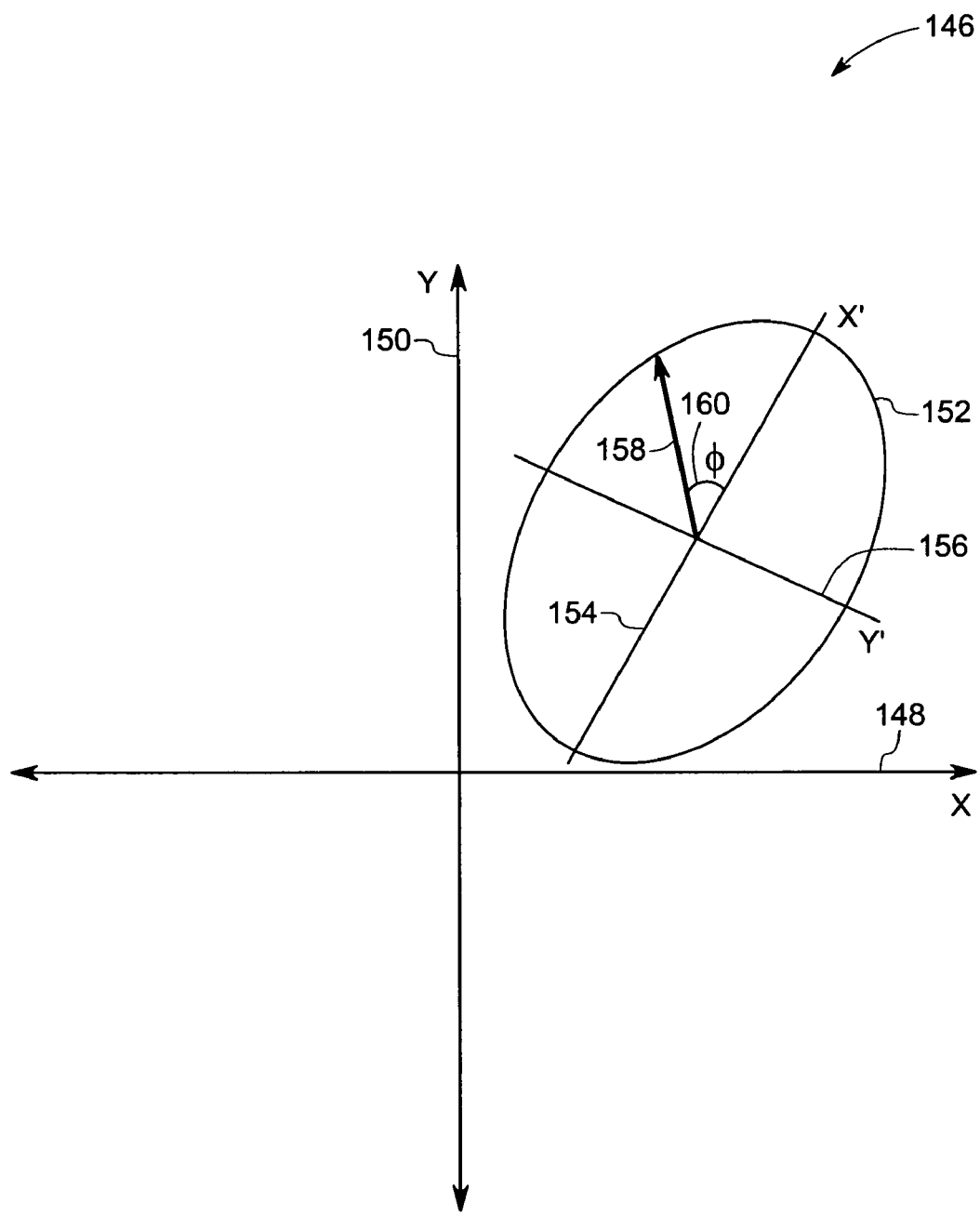
FIG. 7 depicts one technique of extracting periodicity information from CT projection data, in accordance with aspects of the present technique.

In accordance with the PCA technique, the two-dimensional center of mass data may be plotted to track the movement of the center of cardiac mass. FIG. 7 illustrates a plot 146, and the axes x 148 and y 150 of the coordinate system used in the analysis of the center of the mass. In this embodiment the plot of the x component and the y component of the center of mass data as a function of time may comprise a shape of an ellipse 152. Further, a principal axis 154 of the ellipse 152 may be identified by locating the axis along which the center of mass data is primarily distributed. In addition, the center of mass data may be projected onto the principal axis 154 that may result in reducing the dimensionality of the center of mass data set while retaining as much information as is possible. The projected motion signal may then be employed in lieu of the ECG signal. Further, the periodicity information of the cardiac cycle may be extracted from the projection motion signal as described hereinabove.

Alternatively, in another implementation of the present technique, the projection of the center of mass data onto the principal axis 154 may be avoided by following the phase information φ 160 associated with each of the points on the ellipse. Referring to FIG. 7, a new coordinate system can be determined by axes (x', y'). Axis x' may lay along the principal axis of the ellipse formed by the center of mass points as tracked in time, and y' 156 the axis orthogonal to x'. Each center of mass point in time can be represented by a vector $\vec{c}$ 158 in the new coordinate system (x',y') as:

$$\vec{c}(t) = \alpha(t) e^{j\phi(t)} \quad (22)$$

where α is the amplitude of the vector $\vec{c}(t)$, and φ the phase.

The phase information φ 160 associated with the vector $\vec{c}(t)$ 158 may be calculated and tracked around the origin (x',y') and denotes the central moment of the center of mass calculations. Tracking the phase information φ 160 from about 0° to about 360° determines a period of the cardiac motion.

In another embodiment, the phase φ 160 may be estimated by assuming a parametric model for $\vec{c}(t)$ 158. The phase φ 160 varies in time from about 0° to about 360°. Therefore, φ(t) is a cyclic function of time. However, for a steady heart rate φ(t) is periodic. As will be appreciated, a pre-determined phase P, which may represent an offset of P % from a maxima of a cardiac period, intersects with φ(t) at instances of times when the phase of the vector $\vec{c}(t)$ 158 is substantially equal to the pre-determined phase P. In one embodiment, projection data centered around instances of time where the pre-determined phase P is substantially equal to the phase of the vector $\vec{c}(t)$ 158 may be selected for reconstruction. This approach does not require PCA, and utilizes the phase φ(t) information for the reconstruction.

Figure 8:
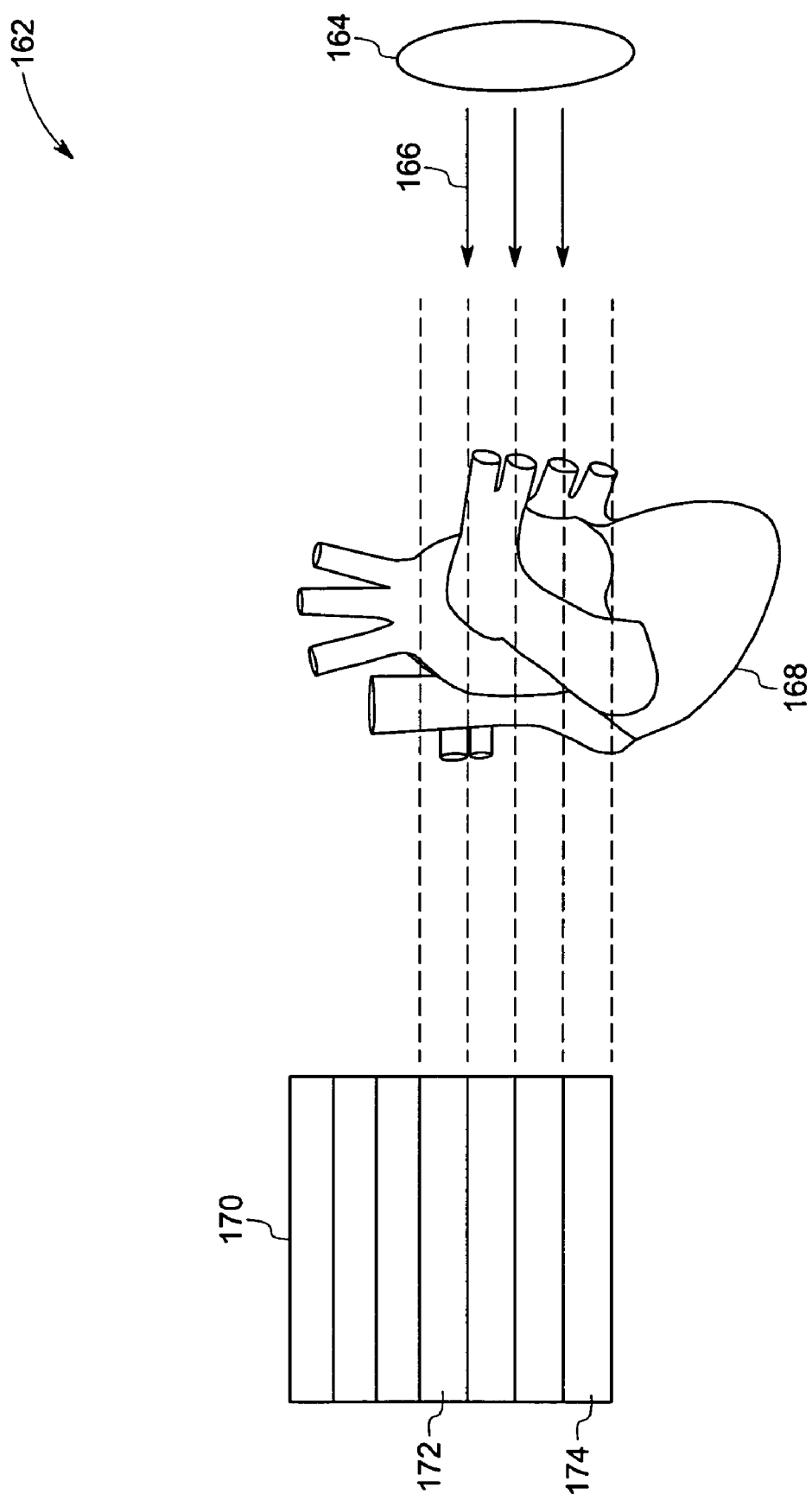
FIG. 8 is an illustration of an alternate embodiment of extracting periodicity information from CT projection data, in accordance with aspects of the present technique.

An additional embodiment 162 of the present technique is depicted in FIG. 8. In this embodiment, a source 164 may be employed to generate X-rays 166 in order to scan an object, such as the heart 168, as discussed above. Further, a multi-row detector 170 may be employed to collect the projection data attenuated by the heart. In one implementation employing the multi-row detector 170, projection data is only acquired by a middle row 172 of the detector 170. In this implementation, it may be difficult to measure or estimate cardiac motion when the middle row 172 is positioned such that it acquires projection data corresponding to the base or apex of the heart 168, such as during the beginning or end of a helical scan of the heart 168. In particular, the base or apex of the heart 168 undergoes relatively little motion and so it is more difficult to accurately estimate motion from the projection data in accordance with the techniques disclosed herein.

In one embodiment, this situation is addressed by refraining from estimating motion from the projection data corresponding to the base or apex of the heart 168, and only estimating the motion when portion of the heart 168 undergoing stronger motion, i.e., an interior region, is being scanned by the middle row 172 of the detector 170. For example, cardiac motion may not be estimated or measured until 4 or 5 seconds have elapsed in the cardiac scan, allowing the middle row 172 of the detector 170 to proceed past the base of the heart 168. If desired, an extrapolation may be performed to estimate the motion of the heart 168 at the beginning and end of the scan, such as during the initial 4 or 5 seconds, so that the motion estimate is complete.

Alternately, in another embodiment, projection data may be acquired from a row of the multi-row detector 170 aligned with a region of the heart 168 undergoing more motion. For example, one of the end rows 174, i.e., the first and last rows, is typically aligned with a more interior (and more dynamic) region of the heart 168 when the middle row 172 is aligned with the base or apex of the heart 168. Projection data may be acquired from the end row aligned with a more interior region of the heart 168 when the middle row 172 is aligned with the base of the heart 168. The projection data acquired from the end row 174 may then be used to extract the center of mass motion in conjunction with the projection data from middle detector row 172. This embodiment estimates an approximation of the center of mass motion at the same time instance, but at a different location where there is stronger cardiac motion. This is used to avoid the weak signal at the edges due to the weak cardiac motion that the center row detects at the base and apex of the heart 168.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A method for extracting information of a cardiac cycle from projection data, the method comprising:
    acquiring one or more sets of computed tomography (CT) projection data;
    analyzing the one or more sets of CT projection data to obtain a center of cardiac mass;
    estimating raw motion data by tracking the center of cardiac mass over time, selecting a window of CT projection data, estimating the center of mass of the selected window of CT projection data, shifting the window by a pre-determined amount to envelope an adjacent set of CT projection data, and estimating the center of mass of the adjacent set of CT projection data;
    processing the raw motion data to extract a motion signal from the raw motion data; and
    extracting the periodicity information from the motion signal.

2. The method of claim 1, wherein acquiring the set of CT projection data comprises acquiring projection data via one of a multi-slice CT detector system or a volumetric CT detector system.

3. The method of claim 1, wherein each of the one or more sets of CT projection data comprises a set of cardiac CT projection data.

4. The method of claim 1, wherein analyzing each of the one or more sets of projection data comprises calculating at least one of a zero order moment, a first order moment, or a second order moment of the set of projection data.

5. The method of claim 4, wherein analyzing each of the one or more sets of projection data comprises computing an estimate of the center of mass of each of the one or more sets of projection data employing the at least one set of zero order moments, first order moments, and second order moments of the set of projection data.

6. The method of claim 5, wherein computing the estimate of the center of mass comprises employing a least square fitting.

7. The method of claim 6, wherein computing the estimate of the center of mass further comprises processing the estimate of the center of mass to remove a low frequency fluctuation.

8. The method of claim 7, wherein removing the low frequency fluctuation comprises removing a shift in a mean signal which comprises processing the center of mass estimate via a low pass filter.

9. The method of claim 1, wherein extracting the motion signal from the raw motion data comprises removing a noise component from the raw motion data.

10. The method of claim 9, wherein extracting the motion signal comprises applying one of a short-time Fourier transform, a continuous Wavelet transform, or a RST Fourier transform to the raw motion data.

11. The method of claim 1, wherein extracting the periodicity information from the motion signal comprises estimating a first order derivative and a second order derivative of the motion signal.

12. The method of claim 11, further comprising employing the first order derivative and the second order derivative to identify a plurality of inflection points.

13. The method of claim 12, wherein the plurality of inflection points comprises a maxima and a minima.

14. The method of claim 12, wherein the plurality of inflection points comprises a zero crossing.

15. The method of claim 1, wherein the motion signal is a cardiac motion signal.

16. The method of claim 15, further comprising reconstructing one or more images based upon the motion signal.

17. A method for extracting information regarding cyclical motion, the method comprising:
   acquiring one or more sets of computed tomography (CT) projection data;
   estimating raw motion data representative of the motion of the center of mass from the one or more sets of CT projection data; by extracting a motion signature by plotting the two-dimensional center of mass data along a principal axis, wherein the projected data is employed as a pseudo-electrocardiogram signal and
   extracting the periodicity information from the raw motion data.

18. The method of claim 17, comprising gated reconstruction of a cardiac image using the motion signature, which can be used in place of an electrocardiogram signal for gated reconstructions of the heart.

19. The method of claim 17, wherein extracting the motion signature comprises extracting the motion signature from the center of mass data via principal component analysis.

20. The method of claim 17, further comprising tracking the phase of the center of mass vector to extract periodicity information.

21. The method of claim 17, wherein extracting the periodicity information comprises locating at least one of a minima, maxima or zero crossings on the waveform of the extracted motion signature.

22. The method of claim 17, wherein acquiring the one or more sets of CT projection data comprises acquiring CT projection data from at least an end row of a multi-row detector.

23. The method of claim 22, wherein acquiring the one or more sets of CT projection data comprises acquiring CT projection data from the end row and a middle row of the multi-row detector.

24. The method of claim 17, wherein acquiring the one or more sets of CT projection data comprises acquiring CT projection data from at least a row of a multi-row detector aligned with a region of a heart undergoing more motion than an end region of the heart.

25. The method of claim 17, wherein acquiring the one or more sets of CT projection data comprises acquiring CT projection data for a region of a heart excluding at least one end of the heart.

26. The method of claim 25, wherein estimating the motion signal comprises extrapolating an estimated motion signal for the at least one end of the heart from a measured motion signal for the region of the heart.

27. The method of claim 25, wherein estimating the motion signal comprises extrapolating an estimated motion signal for a region of the heart from a measured motion signal for another region of the heart.

28. A computer readable medium storing a computer program comprising:
   code adapted to acquire one or more sets of computed tomography (CT) projection data;
   code adapted to analyze the one or more sets of CT projection data to obtain a center of cardiac mass;
   code adapted to estimate raw motion data by tracking the center of cardiac mass over time, selecting a window of CT projection data;
   estimating the center of mass of the selected window of CT projection data, shifting the window by a pre-determined amount to envelope an adjacent set of CT projection data, and estimating the center of mass of the adjacent set of CT projection data;
   code adapted to process the raw motion data to extract a motion signal from the raw motion data; and
   code adapted to extract the periodicity information from the motion signal.

29. The computer readable medium, as recited in claim 28, wherein the code adapted to acquire the set of CT projection data comprises acquiring projection data via one of a multi-slice CT detector system or a volumetric CT detector system.

30. The computer readable medium, as recited in claim 28, wherein each of the one or more sets of CT projection data comprises a set of cardiac CT projection data.

31. The computer readable medium, as recited in claim 28, wherein the code adapted to analyze each of the one or more sets of projection data comprises calculating at least one of a zero order moment, a first order moment, or a second order moment of the set of projection data.

32. The computer readable medium, as recited in claim 31, wherein the code adapted to analyze each of the one or more sets of projection data comprises computing an estimate of the center of mass of each of the one or more sets of projection data employing the at least one set of zero order moments, first order moments, and second order moments of the set of projection data.

33. The computer readable medium, as recited in claim 32, wherein the code adapted to compute the estimate of the center of mass comprises employing a least square fitting.

34. The computer readable medium, as recited in claim 33, wherein the code adapted to compute the estimate of the center of mass further comprises processing the estimate of the center of mass to remove a low frequency fluctuation.

35. The computer readable medium, as recited in claim 28, wherein the code adapted to remove the low frequency fluctuation comprises removing a shift in a mean signal which comprises processing the center of mass estimate via a low pass filter.

36. The computer readable medium, as recited in claim 28, wherein the code adapted to extract the motion signal from the raw motion data comprises removing at least one of noise components or high frequency components from the raw motion data.

37. The computer readable medium, as recited in claim 36, wherein the code adapted to extract the motion signal comprises applying one of a short-time Fourier transform, a continuous Wavelet transform, or a RST Fourier transform to the raw motion data.

38. The computer readable medium, as recited in claim 28, wherein the code adapted to extract the motion signal from the raw motion data comprises tracking time-varying heart cycles from the raw motion data.

39. The computer readable medium, as recited in claim 28, wherein the code adapted to extract the periodicity information from the motion signal comprises estimating a first order derivative and a second order derivative of the motion signal.

40. The computer readable medium, as recited in claim 39, further comprising code adapted to employ the first order derivative and the second order derivative to identify a plurality of inflection points.

41. The computer readable medium, as recited in claim 28, further comprising code adapted to reconstruct one or more images based upon the motion signal.

42. A computer readable medium storing a computer program comprising:
code adapted to acquire one or more sets of computed tomography (CT) projection data; by extracting a motion signature by plotting the two-dimensional center of mass data along a principal axis, wherein the projected data is employed as a pseudo-electrocardiogram signal;
code adapted to estimate raw motion data representative of the motion of the center of cardiac mass from the one or more sets of CT projection data; and
code adapted to extract the periodicity information from the raw motion data.

43. The computer readable medium, as recited in claim 42, comprising code adapted to perform gated reconstruction of a cardiac image using the motion signature, which can be used in place of an electrocardiogram signal for gated reconstructions of the heart.

44. The computer readable medium, as recited in claim 42, wherein the code adapted to extract the motion signature comprises extracting the motion signature from the center of mass data via principal component analysis.

45. The computer readable medium, as recited in claim 42, further comprising code adapted to track the phase of the center of mass vector to extract periodicity information.

46. The computer readable medium, as recited in claim 42, wherein the code adapted to extract the periodicity information comprises locating at least one of a minima, maxima or zero crossings on the waveform of the extracted motion signature.

47. The computer readable medium, as recited in claim 42, further comprising code adapted to compute a center of mass of the motion signature.

48. The computer readable medium, as recited in claim 42, wherein the code adapted to acquire the one or more sets of CT projection data comprises acquiring CT projection data from at least a row of a multi-row detector aligned with a region of a heart undergoing more motion than an end region of the heart.

49. The computer readable medium, as recited in claim 42, wherein the code adapted to estimate the motion signal comprises extrapolating an estimated motion signal for the at least one end of the heart from a measured motion signal for the region of the heart.

50. The computer readable medium, as recited in claim 42, wherein the code adapted to estimate the motion signal comprises extrapolating an estimated motion signal for a region of the heart from a measured motion signal for another region of the heart.

51. A CT imaging system, the system comprising:
a X-ray source configured to emit a stream of radiation;
an area detector configured to detect the stream of radiation and to generate one or more signals responsive to the stream of radiation, wherein the detector comprises a plurality of detector elements;
a system controller configured to rotate the X-ray source and the area detector and to acquire one or more sets of projection data from one or more of the detector elements via a data acquisition system; and
a computer system configured to receive the set of projection data, to analyze the one or more sets of projection data to obtain a center of cardiac mass data, to estimate raw motion data representative of a motion of the center of cardiac mass from the one or more sets of projection data, to extract a motion signal from the raw motion data by separating the motion signal from a noise, and to extract a periodicity information from the motion signal.

52. The CT imaging system of claim 51, wherein the detector comprises one of a multi-slice CT detector system or a volumetric CT detector system.

53. The CT imaging system of claim 51, wherein the detector comprises a volumetric CT detector.

54. The CT imaging system of claim 51, wherein the set of projection data comprises a set of cardiac projection data.

55. The CT imaging system of claim 51, wherein the motion signal is a cardiac motion signal.

56. The CT imaging system of claim 55, wherein the computer system is further configured to reconstruct one or more images based upon the motion signal.

57. A CT image analysis system, the system comprising:
means for analyzing the one or more sets of projection data to obtain a center of cardiac mass data;
means for estimating raw motion data representative of a motion of the center of cardiac mass from the one or more sets of projection data;
means for extracting a motion signal from the raw motion data via separating the motion signal from a noise; and
means for extracting a periodicity information from the motion signal.

* * * * *

UNITED STATES PATENT AND TRADEMARK OFFICE
CERTIFICATE OF CORRECTION

PATENT NO. : 7,477,771 B2
APPLICATION NO. : 11/003114
DATED : January 13, 2009
INVENTOR(S) : Iatrou et al.

It is certified that error appears in the above-identified patent and that said Letters Patent is hereby corrected as shown below:

Title Page, Item (73), "Assignee", delete "Genral" and insert -- General --, therefor.

Title Page, Item (57), "ABSTRACT", after "one or" insert -- more --, therefor.

In Column 9, Lines 54-55, in Equation (16), delete " $\frac{1}{D^2 + r^22 + rD\sin(\beta - \phi)} = $ " and insert -- $\frac{1}{D^2 + r^2 + 2rD\sin(\beta - \phi)} = $ --, therefor.

Signed and Sealed this

Thirtieth Day of November, 2010

David J. Kappos
*Director of the United States Patent and Trademark Office*